(12) United States Patent
Wen et al.

(10) Patent No.: US 12,145,932 B2
(45) Date of Patent: Nov. 19, 2024

(54) METHOD OF MANUFACTURING A SOLID FORM OF A BET BROMODOMAIN INHIBITOR

(71) Applicant: ZENITH EPIGENETICS LTD., Calgary (CA)

(72) Inventors: Feng Wen, Shanghai (CN); Jiahui Chen, Shanghai (CN); Xianghui Wen, Shanghai (CN); Mark T. Edgar, Rancho Santa Fe, CA (US); Henrik C. Hansen, Calgary (CA)

(73) Assignee: ZENITH EPIGENETICS LTD., Calgary (CA)

( * ) Notice: Subject to any disclaimer, the term of this patent is extended or adjusted under 35 U.S.C. 154(b) by 768 days.

(21) Appl. No.: 17/275,465

(22) PCT Filed: Sep. 13, 2019

(86) PCT No.: PCT/IB2019/001011
§ 371 (c)(1),
(2) Date: Mar. 11, 2021

(87) PCT Pub. No.: WO2020/053657
PCT Pub. Date: Mar. 19, 2020

(65) Prior Publication Data
US 2022/0048905 A1  Feb. 17, 2022

Related U.S. Application Data

(60) Provisional application No. 62/730,849, filed on Sep. 13, 2018.

(51) Int. Cl.
*C07D 471/04* (2006.01)
*B01J 23/44* (2006.01)

(52) U.S. Cl.
CPC ............ *C07D 471/04* (2013.01); *B01J 23/44* (2013.01); *C07B 2200/13* (2013.01)

(58) Field of Classification Search
CPC .................................................. C07D 471/04
See application file for complete search history.

(56) References Cited

U.S. PATENT DOCUMENTS

| | | | |
|---|---|---|---|
| 9,663,520 B2 * | 5/2017 | Quinn | A61P 9/10 |
| 10,010,556 B2 | 7/2018 | Quinn et al. | |
| 2012/0208814 A1 | 8/2012 | Demont et al. | |
| 2016/0159801 A1 | 6/2016 | Quinn et al. | |
| 2022/0047563 A1 | 2/2022 | Campeau et al. | |
| 2022/0048905 A1 | 2/2022 | Wen et al. | |
| 2022/0117942 A1 | 4/2022 | Attwell et al. | |

FOREIGN PATENT DOCUMENTS

| | | |
|---|---|---|
| WO | WO 2015/002754 A2 | 1/2015 |
| WO | WO 2015/004533 A2 | 1/2015 |
| WO | WO 2015/074064 A2 | 5/2015 |
| WO | WO 2016/097870 A1 | 6/2016 |
| WO | WO 2018/097977 A1 | 5/2018 |
| WO | WO 2020/053657 A1 | 3/2020 |
| WO | WO 2020/056232 A1 | 3/2020 |

OTHER PUBLICATIONS

Brittain, Harry G. Polymorphism in Pharmaceutical Solids. Drugs and the Pharmaceutical Sciences, 192. 2009. pp. 76-138.
Bavin, M., Process Development—Polymorphism in Process Development, *Chemistry & Industry*, Aug. 21, 1989, pp. 527-529, 3 pgs.
Caira, M. R., "Crystalline Polymorphism of Organic Compounds," *Topics in Current Chemistry*, vol. 198, Department of Chemistry, University of Cape Town, Copyright: Springer Verlag, Berlin Heidelberg 1998, 46 pgs.
Censi, R. et al., "Polymorph Impact on the Bioavailability and Stability of Poorly Soluble Drugs," *Molecules*, Oct. 15, 2015, vol. 20, No. 10, pp. 18759-18776, received Sep. 11, 2015, accepted Oct. 8, 2015, and published Oct. 15, 2015,18 pgs.
Lee, E. H., "A Practical Guide to Pharmaceutical Polymorph Screening & Selection," *Asian Journal of Pharmaceutical Sciences*, May 16, 2014, vol. 9, No. 4, pp. 163-175, Copyright 2014 Shenyang Pharmaceutical University, 13 pgs.
Newman, A., "Specialized Solid Form Screening Techniques," *Organic Process Research & Development*, ACS Publications, Copyright 2012 American Chemical Society, pp. 457-471, 15 pgs.

* cited by examiner

*Primary Examiner* — David K O'Dell
(74) *Attorney, Agent, or Firm* — FINNEGAN, HENDERSON, FARABOW, GARRETT & DUNNER LLP

(57) ABSTRACT

The invention relates to solid crystalline forms of Compound (I), such as e.g., Form VII, including pharmaceutical compositions thereof and processes for preparing crystalline Compound (I), Form VII. Compound (I) modulates or inhibits the activity of BET bromodomain-containing proteins, and is useful in the treatment of diseases such as cancer, inflammatory and cardiovascular diseases.

(I)

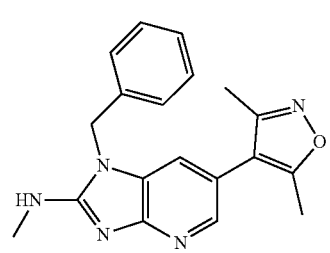

21 Claims, 4 Drawing Sheets

METHOD OF MANUFACTURING A SOLID FORM OF A BET BROMODOMAIN INHIBITOR

This application is a U.S. national phase entry under 35 U.S.C. § 371 of International Application No. PCT/IB2019/001011, filed Sep. 13, 2019, which claims the benefit of priority of U.S. Provisional Application No. 62/730,849, filed Sep. 13, 2018, all of which are incorporated herein by reference in their entirety.

The disclosure relates to solid forms of Compound I (1-benzyl-6-(3,5-dimethylisoxazol-4-yl)-N-methyl-1H-imidazo[4,5-b]pyridine-2-amine) that modulate or inhibit the activity of BET bromodomain-containing proteins, including methods of manufacturing thereof, intermediates in the manufacturing thereof, and pharmaceutical compositions thereof, where Compound I is useful in the treatment of diseases such as cancer.

BACKGROUND

Therapeutic agents that modulate or inhibit the activity of BET bromodomain-containing proteins such as BRD2, BRD3, BRD4, and BRDT have the potential to cure, treat, or improve the lives of patients suffering from diseases such as cancer, autoimmune, and cardiovascular diseases. In particular, BET bromodomain modulators or inhibitors have the potential to treat B-acute lymphocytic leukemia, Burkitt's lymphoma, Diffuse large cell lymphoma, Multiple myeloma, Primary plasma cell leukemia, Lung cancer, Bladder cancer, Breast cancer, Cervix cancer, Colon cancer, Gastric cancer, Glioblastoma, Prostate cancer, Ovarian cancer, and Neuroblastoma among others. Compounds for the treatment of such diseases and conditions are disclosed in PCT Publication No. WO 2015/002754, the disclosure of which is incorporated herein by reference in its entirety.

There is a large unmet need for compounds, including solid forms of derivatives of benzimidazole with high purity. Compounds that in addition to being efficacious also exhibit improved stability, solubility, and a pharmacokinetic and pharmacodynamics profile favorable for the treatment of diseases modulated by BET proteins containing bromodomains, and, importantly, can be made efficiently on a large scale to facilitate clinical and commercial use.

SUMMARY

Compound I is known to modulate or inhibit BET activity and is described in WO 2015/002754. Compound I has the formula:

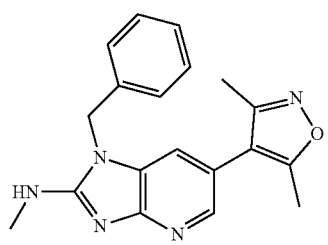

Compound I

The disclosure provides a solid form of Compound I, as well as methods for making the disclosed solid form of Compound I, intermediates used in its manufacture, pharmaceutical compositions comprising crystalline forms of Compound I, and methods for using such forms and pharmaceutical compositions in the treatment of diseases mediated by BET proteins. The details of one or more embodiments are set forth in the description below. Other features, objectives, and advantages will be apparent from the description and from the claims.

DETAILED DESCRIPTION

Figure 1:
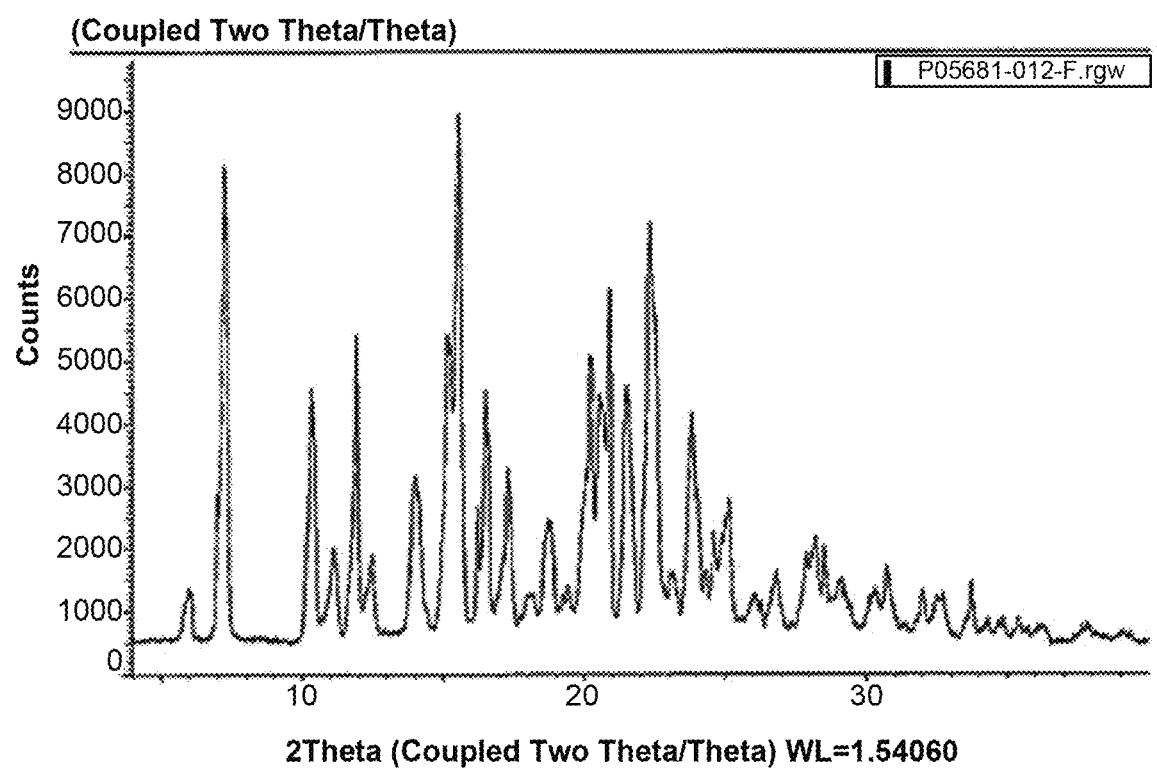
FIG. 1 shows an X-ray powder diffractogram (XRPD) of Compound I—Form VII.

The disclosure provides a process of preparing Compound I that is suitable for scale up and manufacturing on large scale. A process of preparing Compound I is described in WO 2015/002754, which herein is incorporated by reference in its entirety, and particularly for its description of Compound I and its synthesis. In comparison to the synthesis described in WO 2015/002754, the process provided herein has certain advantages that make it suitable for scale-up of the preferred polymorphic form of Compound I (Form VII). For example, the process described herein uses less hazardous reagents, lower reaction temperatures, reagents better suited for scale-up, simplified work-up procedures, and streamlined isolation of intermediates by elimination of purification by column chromatography. All of these factors result in a manufacturing process that is better than prior methods in efficiency and quality, reduced environmental footprint, and reduced cost.

In some embodiments, the process of preparing Compound I comprises starting materials A and G and intermediates B, C, D, E, and F:

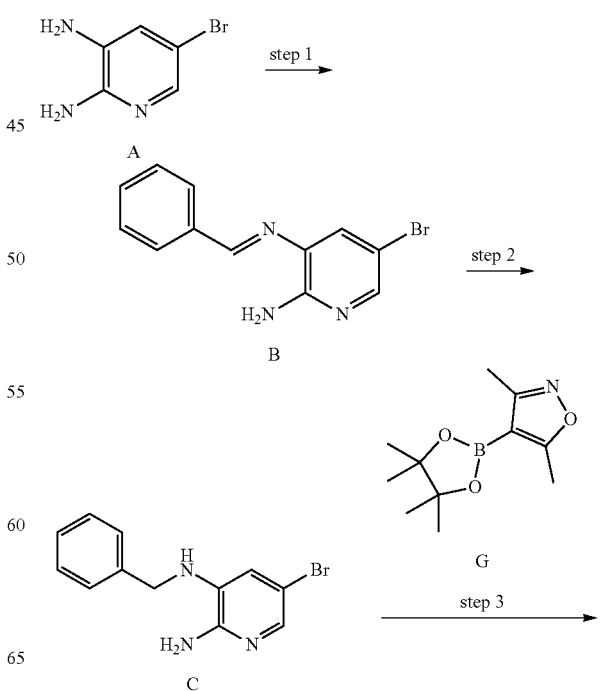

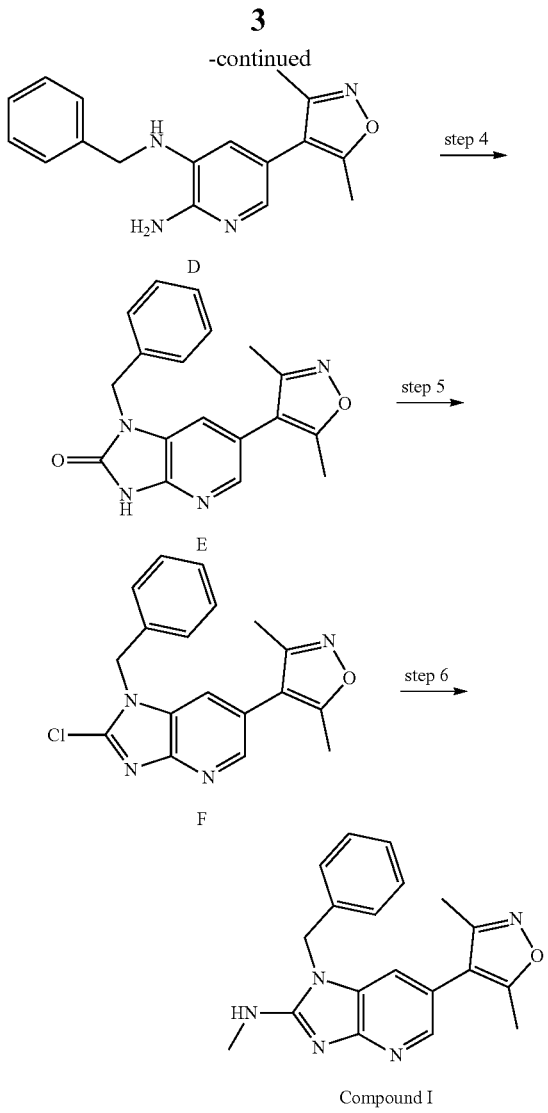

In some embodiments, the process of preparing Compound B comprises reacting Compound A (Step 1):

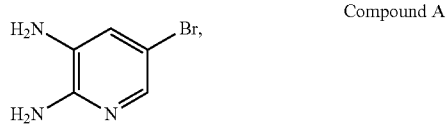

Compound A with benzaldehyde in the presence of an acid. In some embodiments, the acid is acetic acid.

In some embodiments, step 1 is carried out in the presence of a solvent. In some embodiments, the solvent is methanol. In some embodiments, the solvent is ethanol. The use of methanol or ethanol as a solvent in step 1 provides a more efficient work up and isolation by eliminating the need for column chromatography.

In some embodiments of step 1, NaHCO₃ solution is added to the reaction mixture after reaction completion, resulting in precipitation of the product, which simplifies the isolation and purification of Compound B.

In some embodiments of step 1, Compound A and benzaldehyde are used in a 1:1 molar ratio.

In some embodiments, step 1 is conducted at a reduced temperature, and in some embodiments, the reaction temperature is 0-5° C., or below 10° C., or below 20° C.

In some embodiments, the process of preparing Compound C comprises reacting Compound B (Step 2):

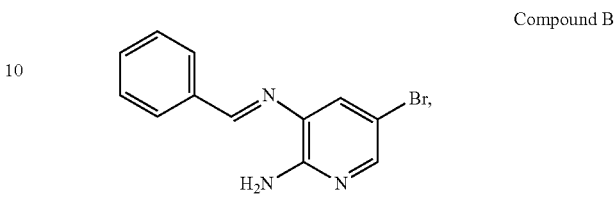

Compound B with NaCNBH₃ or NaBH₄ in a solvent. In some embodiments, the solvent is an alcohol. In some embodiments, the solvent is methanol or ethanol.

In some embodiments, the solvent is ethanol, allowing for a reduction of the loading of NaCNBH₃ or NaBH₄ to 0.6 molar equivalents relative to Compound B, making the process more environmentally friendly and reducing the overall cost.

In some embodiments, the loading of NaCNBH₃ or NaBH₄ is equal to or less than one equivalent relative to Compound B, such as less than 0.9 equivalents, or less than 0.75 equivalents, or equal to or less than 0.6 equivalents relative to Compound B.

In some embodiments of Step 2, the work-up and isolation is done by adding an HCl solution to quench the reaction followed by addition of water to precipitate the product (Compound C) in high purity (+95%), thereby simplifying the work-up and isolation process. In some embodiments, other agents can be used to quench the reaction, such as water or acetic acid.

In some embodiments, Step 2 is carried out at 10-40° C., or 15-20° C., or 20-25° C.

In some embodiments, the process of preparing Compound D comprises reacting Compound C (Step 3):

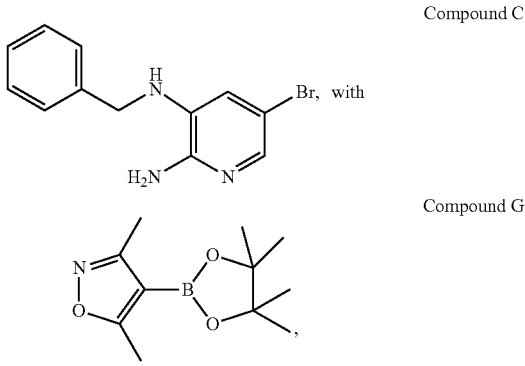

in the presence of a transition metal catalyst and a base, wherein the transition catalyst is a palladium catalyst.

In some embodiments, the palladium catalyst is [1,1'-bis(diphenylphosphino)ferrocene]dichloropalladium(II) (Pd(dppf)Cl₂, dichloro(bis{di-tert-butyl[4-(dimethylamino)phenyl]phosphoranyl})palladium (PD-132), or tetrakis(tri(o-tolyl)phosphine)palladium(0).

In some embodiments the palladium catalyst is Pd(PPh₃)₄.

In some embodiments, the base is CsF. In some embodiments, the base is an alkali metal carbonate. In some embodiments, the base is $K_2CO_3$. In some embodiments, the base is an alkali metal phosphate. In some embodiments, the base is $K_3PO_4$.

The use of $K_3PO_4$ is advantageous, compared to $K_2CO_3$, since $K_3PO_4$ is well dispersed in the reactor and thus results in a reaction with less by-products, and the product (Compound D) of higher purity.

In some embodiments, the reaction is carried out in a solvent mixture comprising 1,4-dioxane and water.

In some embodiments, the reaction is carried out at an elevated temperature, such as 80-100° C., or 90-100° C., or 90-95° C.

In some embodiments, the process of preparing Compound E comprises reacting Compound D (Step 4):

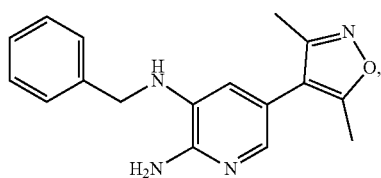

Compound D with carbonyldiimidazole (CDI) in a solvent.

In some embodiments, the solvent is an aprotic solvent. In some embodiments the solvent is 1,4-dioxane, DMSO, or DMF.

The advantage of using DMSO is that it is a safer (Class 3) and more environmentally friendly solvent. The use of DMSO also allowed for the development of a simplified isolation procedure, involving precipitation of the product (Compound E) by addition of water to the reaction mixture. This eliminated a lengthy work-up process, including the use of chromatography, and thus provides Compound E in an efficient manner.

In some embodiments, CDI in a solvent is added potion wise to reduce the heat release during addition to the reaction mixture.

In some embodiments, the reaction is carried out at an elevated temperature, such as 20-70° C., or 30-40° C., or 40-65° C., or 55-60° C.

In some embodiments, the process of preparing Compound F comprises reacting Compound E (step 5):

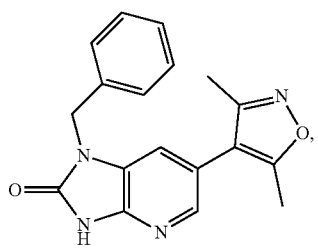

Compound E with a chlorination reagent in the presence of a base.

In some embodiments, the chlorination reagent is phosphoryl chloride ($POCl_3$).

In some embodiments, $POCl_3$ is used in excess (2-30 molar equivalents relative to Compound E, or 4-7 equivalents, or 5-15 equivalents, or 7-10 equivalents).

In some embodiments, the base is an amine base.

In some embodiments, the amine base is N,N-diisopropylethylamine (DIPEA). In some embodiments, the amine base is trimethylamine or N, N-dimethylaniline.

In some embodiments, DIPEA was used in excess (1.01-10 molar equivalents relative to Compound E, or 1.01-3 equivalents, or 5-10 equivalents).

In some embodiments, 4-5 molar equivalents, or 8-9 molar equivalents of $POCl_3$ relative to Compound E and 1.0-1.1 molar equivalents, or 2.5 molar equivalents of DIPEA are used relative to Compound E, reducing the formation of unwanted byproducts and simplifying the purification process of Compound E.

In some embodiments, step 5 is carried out at an elevated temperature such as 95-100° C. or 80-100° C.

In some embodiments, Step 5 further comprises co-distillation of the crude reaction mixture with ethyl acetate. This is used as an efficient method to remove excess $POCl_3$ from the reaction mixture prior to quenching the reaction with $NaHCO_3$ solution.

In some embodiments, the product (Compound F) is isolated by crystallization from a mixture of ethyl acetate and non-polar co-solvent. In some embodiments the non-polar co-solvent is hexane, heptane, or toluene.

In some embodiments, the product (Compound F) is isolated by crystallization from an ethyl acetate/n-heptane mixture.

In some embodiments, the process of preparing Compound I comprises reacting Compound F (Step 6):

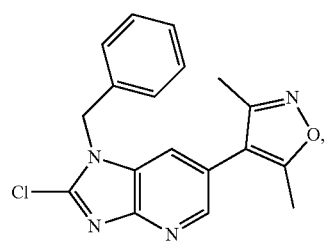

Compound F with methylamine.

In some embodiments, methylamine 2 M in THF is used.

In some embodiments, the reaction is carried out at 20-30° C. This temperature avoids methylamine volatilization and pressure build-up.

In some embodiments, the reaction work-up comprises dissolving the crude product in an aqueous HCl solution (for example 7 N HCl) and washing with a non-polar solvent. In some embodiments, the non-polar solvent is dichloromethane, which efficiently removes remaining impurities from the previous step. Then, the crude product is neutralized with aqueous NaOH solution and the product is isolated.

In some embodiments, the desired form (Form VII) of Compound I was obtained from crystallization from ethanol (EtOH) and methyl tert-butyl ether (MTBE).

In some embodiments, to remove any remaining HCl, the dried Compound I can be dissolved in ethanol, treated with a solution of sodium hydroxide in ethanol, followed by addition of process water to precipitate the product.

In some embodiments, the crystallization was seeded with Compound I—Form VII to ensure formation of the desired polymorph.

In some embodiments, the precipitation is carried out by (1) cooling the ethanol solution of Compound I, (2) adding seed crystals of Compound I—Form VII, (3) stirring the mixture for about 10 h, (4) cooling the mixture further and adding MTBE, (5) stirring for about 3-5 h to precipitate Compound I—Form VII.

In some embodiments, MBTE can be added before the adding seed crystals of Compound I—Form VII.

Disclosed herein is a method of making a crystalline solid form of Compound I. Crystalline forms of the same compound typically have different properties, including hygroscopicity, solubility, and stability. Polymorphs with high melting points often have good thermodynamic stability which is advantageous in prolonging shelf-life for formulations containing the solid form of the compound. Polymorphs with lower melting points are typically less thermodynamically stable, but are favored by increased water solubility, often translating into increased bioavailability for the compound. Weakly hygroscopic polymorphs are often more stable to heat and humidity and resistant to degradation during storage. Anhydrous polymorphs are often favored as they can be consistently made without or with less variation in composition due to varying solvent and water content.

Compound I can be obtained in a solid crystalline form referred to as Form VII. Form VII is an anhydrate. Form VII, a polymorph of Compound I, is characterized by its XRPD and other data. Form VII of Compound I is characterized by an X-ray powder diffractogram (XRPD) comprising a peak, in terms of 2-theta, at 16.5 degrees ±0.2 degrees θ, as determined on a diffractometer using a Cu—$K_\alpha$ radiation tube.

In some embodiments, Form VII of Compound I is characterized by an X-ray powder diffractogram (XRPD) comprising one or more peaks, in terms of 2-theta, at 7.2, 10.3, 11.2, 12.0, 13.8, 13.9, 15.2, 15.6, 16.5, 17.3, 20.7, 20.9, 21.6, and 22.5 degrees, wherein each peak is ±0.2 degrees θ, as determined on a diffractometer using a Cu—$K_\alpha$ radiation tube.

In some embodiments, Form VII of Compound I is characterized by an X-ray powder diffractogram (XRPD) comprising three or more peaks, in terms of 2-theta, at 7.2, 10.3, 11.2, 12.0, 13.8, 13.9, 15.2, 15.6, 16.5, 17.3, 20.7, 20.9, 21.6, and 22.5 degrees, wherein each peak is ±0.2 degrees θ, as determines on a diffractometer using a Cu—$K_\alpha$ radiation tube.

In some embodiments, Form VII of Compound I is characterized by an X-ray powder diffractogram (XRPD) comprising six or more peaks, in terms of 2-theta, at 7.2, 10.3, 11.2, 12.0, 13.8, 13.9, 15.2, 15.6, 16.5, 17.3, 20.7, 20.9, 21.6, and 22.5 degrees, wherein each peak is ±0.2 degrees θ, as determines on a diffractometer using a Cu—$K_\alpha$ radiation tube.

In some embodiments, Form VII of Compound I is characterized by an X-ray powder diffractogram (XRPD) comprising ten or more peaks, in terms of 2-theta, at 7.2, 10.3, 11.2, 12.0, 13.8, 13.9, 15.2, 15.6, 16.5, 17.3, 20.7, 20.9, 21.6, and 22.5 degrees, wherein each peak is ±0.2 degrees θ, as determines on a diffractometer using a Cu—$K_\alpha$ radiation tube.

In some embodiments, Form VII of Compound I is characterized by an X-ray powder diffractogram (XRPD) comprising peaks, in terms of 2-theta, at 7.2, 10.3, 11.2, 12.0, 13.8, 13.9, 15.2, 15.6, 16.5, 17.3, 20.7, 20.9, 21.6, and 22.5 degrees, wherein each peak is ±0.2 degrees θ, as determines on a diffractometer using a Cu—$K_\alpha$ radiation tube.

In some embodiments, Form VII of Compound I is characterized by an X-ray powder diffractogram (XRPD) pattern substantially as shown in FIG. 1, as determines on a diffractometer using a Cu—$K_\alpha$ radiation tube.

In some embodiments, Form VII of Compound I is characterized by a differential scanning calorimetry (DSC) thermogram pattern with an endothermic peak at a temperature of about 205° C.

Figure 2:
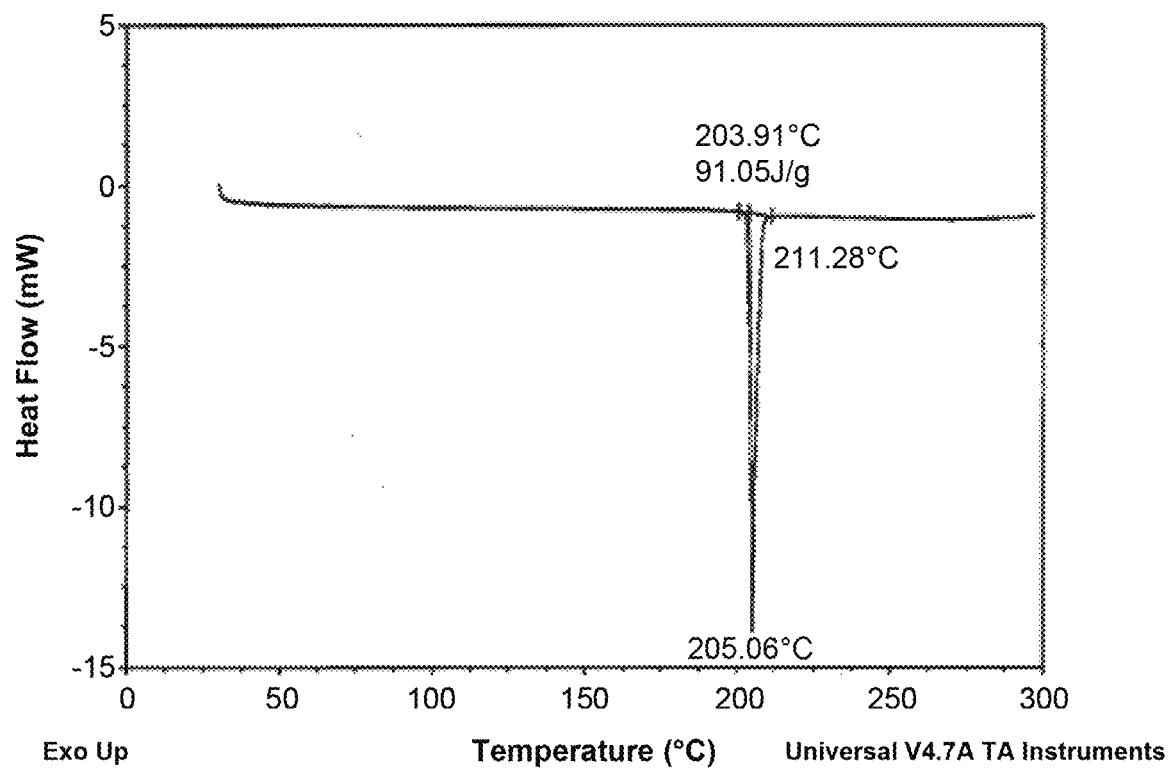
FIG. 2 shows a differential scanning calorimeter (DSC) curve of Compound I—Form VII.

In some embodiments, Form VII of Compound I is characterized by a differential scanning calorimetry (DSC) thermogram pattern substantially as shown in FIG. 2.

Figure 3:
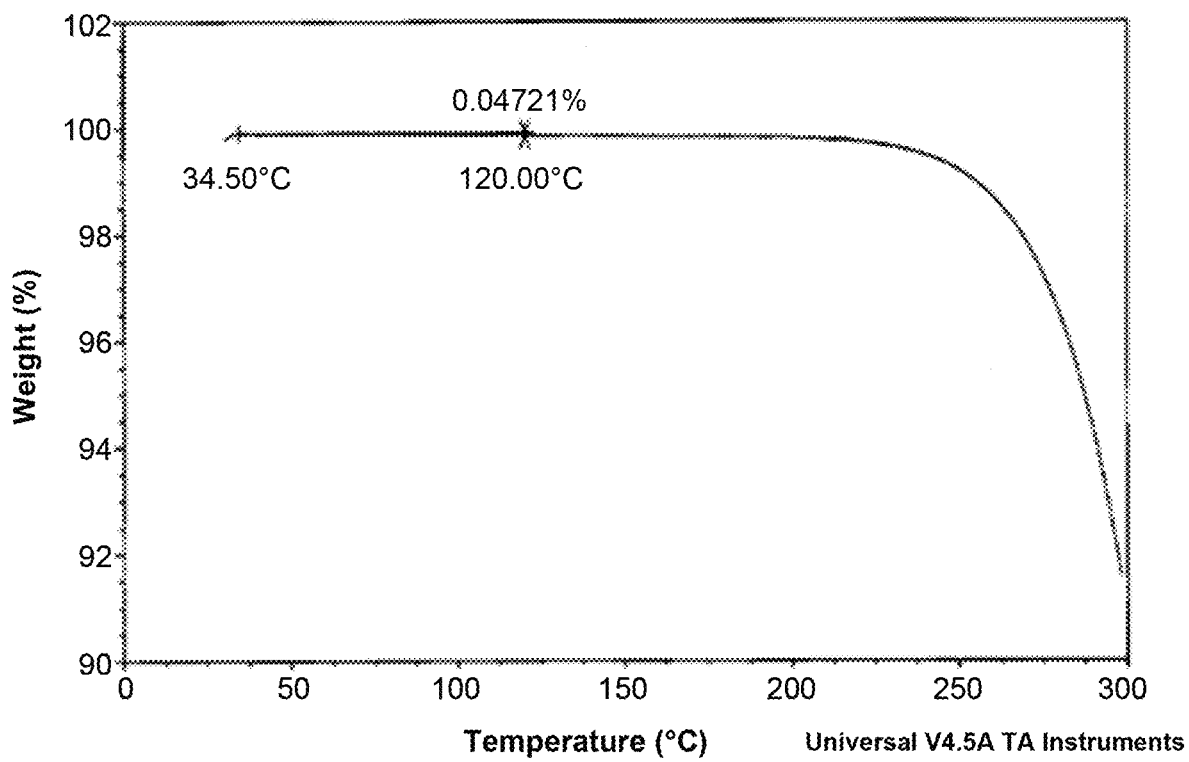
FIG. 3 shows a thermogravimetric analysis (TGA) of Compound I—Form VII.

In some embodiments, Form VII of Compound I is characterized by a thermogravimetric analysis (TGA) thermogram substantially as shown in FIG. 3.

In some embodiments, Form VII of Compound I is characterized by an Infrared (IR) spectrum comprising IR bands at about 3066 $cm^{-1}$ and 1600 $cm^{-1}$.

Figure 4:
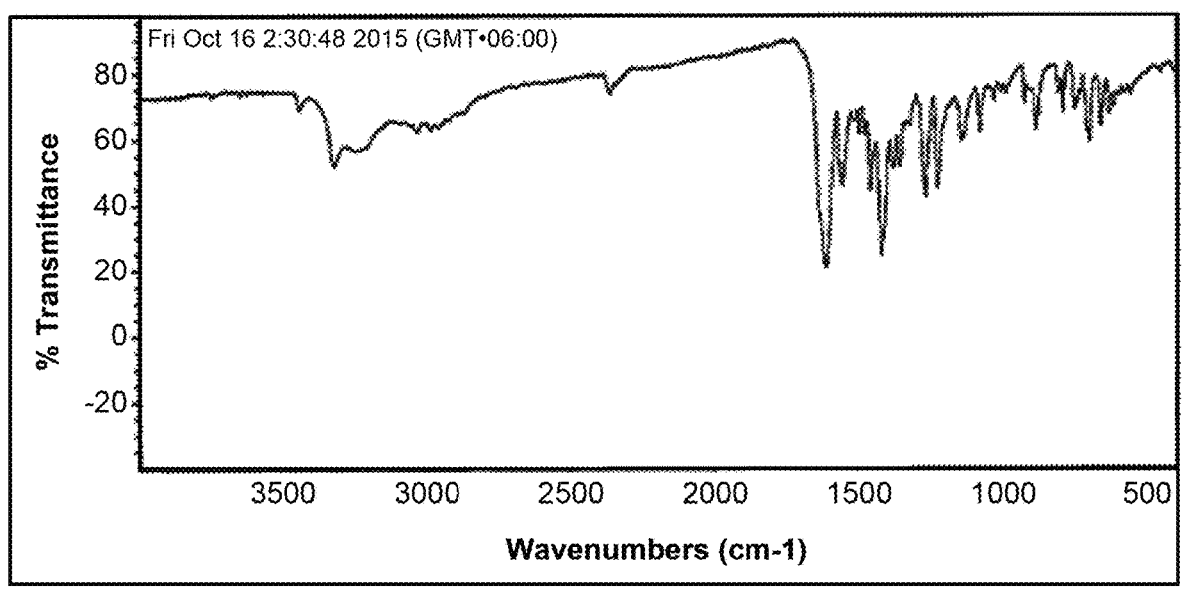
FIG. 4 shows an infrared spectrum (IR) of Compound I—Form VII.

In some embodiments, Form VII of Compound I is characterized by an Infrared (IR) spectrum substantially as shown in FIG. 4.

Also disclosed herein are intermediates useful in the synthesis of BET bromodomain inhibitors, such as Compound B:

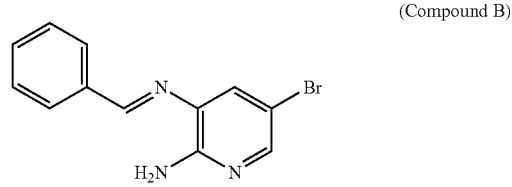 [SMILES: Nc1ncc(Br)cc1/N=C/c1ccccc1]

(Compound B)

and Compound C:

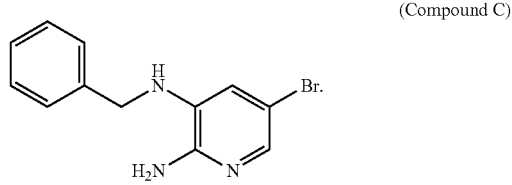 [SMILES: Nc1ncc(Br)cc1NCc1ccccc1]

(Compound C)

In one embodiment, disclosed herein is a method of making a therapeutic agent (Compound I) that modulates or inhibits the activity of BET bromodomain-containing proteins such as BRD2, BRD3, BRD4, and BRDT, which has the potential to cure, treat, or improve the lives of patients suffering from diseases mediated by bromodomain-containing proteins, such as certain cancers, inflammatory diseases, and cardiovascular diseases.

One embodiment is directed to a method of treating a disease that is mediated, at least in part, by BET bromodomain-containing proteins in a subject in need thereof, comprising administrating a therapeutically effective amount of Compound I in crystalline Form VII.

In one embodiment, the disease is selected from cancers, inflammatory diseases, and cardiovascular diseases.

In one embodiment, the disease is a cancer, including B-acute lymphocytic leukemia, Burkitt's lymphoma, diffuse large cell lymphoma, multiple myeloma, primary plasma cell leukemia, lung cancer, bladder cancer, breast cancer, cervical cancer, colon cancer, gastric cancer, glioblastoma, prostate cancer, ovarian cancer, and neuroblastoma.

In one embodiment, the disease is prostate cancer.

In one embodiment, the disease is castration-resistant prostate cancer.

In one embodiment, the disease is metastatic castration-resistant prostate cancer.

In one embodiment, the disease is breast cancer.

In one embodiment, the disease is triple-negative breast cancer.

In one embodiment, the disease is estrogen-receptor positive breast cancer.

In one embodiment, the subject is a human.

When treating a disease, at least in part, mediated by BET bromodomain-containing proteins in a subject in need thereof, the subject may benefit from combination drug treatment. For example, a form or forms of Compound I as described herein may be combined with one or more therapeutic agents in a single composition or in separately administered compositions that may be administered simultaneously, sequentially, or pursuant to a specified treatment regimen.

In one embodiment, a form of Compound I as described herein may be administered sequentially with an additional therapeutic agent(s). Sequentially means that the for or forms of Compound I and the additional therapeutic agent(s) is (are) administered with a time separation of a few seconds (for example 15 sec., 30 sec., 45 sec., 60 sec. or less), several minutes (for example 1 min., 2 min., 5 min. or less, 10 min. or less, 15 min. or less), 1-8 hours, 1-7 days, or 1-4 weeks. When administered sequentially, the form or forms of Compound I as described herein and the additional therapeutic agent(s) may be administered in two or more administrations, and contained in separate compositions or dosage forms, which may be contained in the same or different package or packages.

In one embodiment, a form or forms of Compound I as described herein may be combined with one or more therapeutic agent(s) used to treat cancer.

In one embodiment, Compound I, having Form VII, as described herein, may be combined with one or more therapeutic agent(s) used to treat cancer.

In one embodiment, Compound I, having Form VII, as described herein may be combined with a therapeutic agent selected from an androgen receptor antagonist, an androgen synthesis inhibitor, an aromatase inhibitor, a selective estrogen receptor modulator, a selective estrogen down-regulator, a poly ADP ribose polymerase (PARP) inhibitor, or an immunotherapeutic agent.

In one embodiment, Compound I, having Form VII, as described herein may be combined with a therapeutic agent selected from Abiraterone (Zytiga), Enzalutamide (Xtandi), Apalutamide (ARN-509, Erleada), Darolutamide, Fulvestrant, Exemestane, Talazoparib, Olaperib, Veliparib, Rucaparib, Talazoparib, Niraparib, Pembrolizumab, Nivolumab, Durvalumab, and Rituximab.

A listing of exemplary of embodiments includes:
1. A solid form of a Compound having the formula:

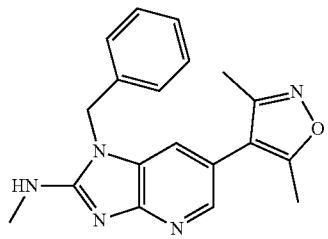

Compound I wherein the solid form is crystalline.

2. The solid form of embodiment 1, which is an anhydrate.

3. The solid form of embodiment 1, wherein the solid form is Form VII.

4. The solid form of embodiment 3, having three or more characteristic XRPD peaks, in terms of 2-theta, at 7.2, 10.3, 11.2, 12.0, 13.8, 13.9, 15.2, 15.6, 16.5, 17.3, 20.7, 20.9, 21.6, and 22.5 degrees, wherein each peak is ±0.2 degrees θ, as determined on a diffractometer using a Cu—$K_\alpha$ radiation tube.

5. The solid form of embodiment 3, having six or more characteristic XRPD peaks, in terms of 2-theta, at 7.2, 10.3, 11.2, 12.0, 13.8, 13.9, 15.2, 15.6, 16.5, 17.3, 20.7, 20.9, 21.6, and 22.5 degrees, wherein each peak is ±0.2 degrees θ, as determined on a diffractometer using a Cu—$K_\alpha$ radiation tube.

6. The solid form of any one of embodiments 1-3, having an XRPD pattern substantially similar to that shown in FIG. 1.

7. The solid form of any one of embodiments 1-6, having a DSC themogram pattern with an endothermic peak at a temperature of about 205° C.

8. The solid form of any of embodiments 1-6 having a DSC thermogram substantially similar to that shown in FIG. 2.

9. The solid form of any of embodiments 1-7 having a TGA thermogram substantially similar to that shown in FIG. 3.

10. A pharmaceutical composition comprising the solid form of any one of embodiments 1-9 and at least one pharmaceutically acceptable carrier.

11. A method of treating a cancer, comprising administrating to a subject in need of such treatment a therapeutically effective amount of the solid form of any one of embodiments 1-9 or the pharmaceutical composition of embodiment 10.

12. The method of embodiment 11, wherein the cancer is B-acute lymphocytic leukemia, Burkitt's lymphoma, diffuse large cell lymphoma, multiple myeloma, primary plasma cell leukemia, lung cancer, bladder cancer, breast cancer, cervical cancer, colon cancer, gastric cancer, glioblastoma, prostate cancer, ovarian cancer, or neuroblastoma.

13. The method of embodiment 12, wherein the cancer is prostate cancer.

14. The method of embodiment 12, wherein the cancer is castration-resistant prostate cancer.

15. The method of embodiment 12, wherein the cancer is metastatic castration-resistant prostate cancer.

16. The method of embodiment 12, wherein the cancer is breast cancer.

17. The method of embodiment 12, wherein the cancer is triple-negative breast cancer.

18. The method of embodiment 12, wherein the cancer is estrogen-receptor positive breast cancer.

19. A method of treating an inflammatory disease, comprising administrating to a patient in need of such treatment a therapeutically effective amount of the solid form of any one of embodiments 1-9 or the pharmaceutical composition of embodiment 10.

20. A method of treating a cardiovascular disease, comprising administrating to a patient in need of such treatment a therapeutically effective amount of the solid form of any one of embodiments 1-9 or the pharmaceutical composition of embodiment 10.

21. The method of embodiment 11, wherein the subject is a human. 22. A process of preparing Form VII of Compound I:

(Compound I)

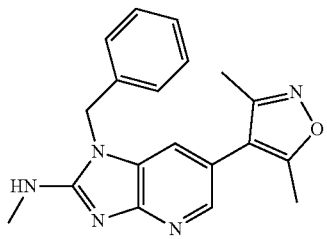

comprising precipitating Form VII from a solution comprising Compound I and one or more solvents.

23. The process of embodiment 22, wherein the solvents are ethanol, t-butylmethylether (MTBE), or a mixture thereof.

24. The process of embodiment 22, wherein the precipitation is carried out by
   (1) cooling the ethanol solution of Compound I;
   (2) adding seed crystals of Compound I—Form VII to the solution;
   (3) stirring the mixture for about 10 h;
   (4) cooling the mixture further and adding MTBE; and
   (5) stirring for about 3-5 h to precipitate Compound I—Form VII.

25. The process of embodiment 24, wherein MTBE is added before the adding the seed crystals of Compound I—Form VII to the mixture.

26. A process of preparing Compound I

Compound I

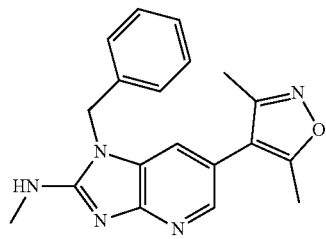

comprising steps (a)-(d):
(a) reacting (Compound C)

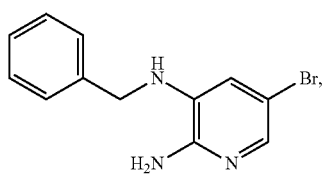

with Compound G:

(Compound G)

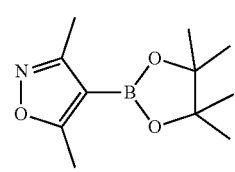

to produce Compound D:

Compound D

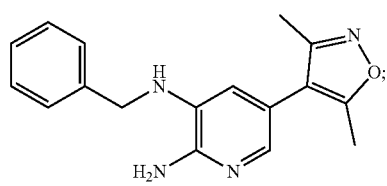

(b) reacting Compound D:

(Compound D)

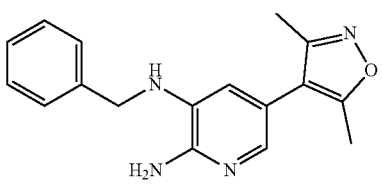

with a first reagent to produce Compound E:

(Compound E)

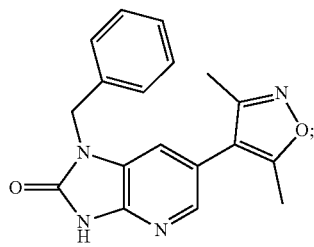

(c) reacting Compound E:

(Compound E)

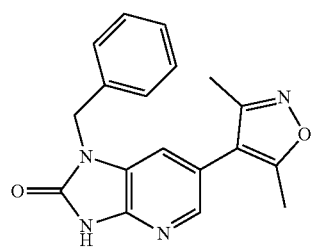

with a chlorination agent to produce Compound F:

(Compound F)

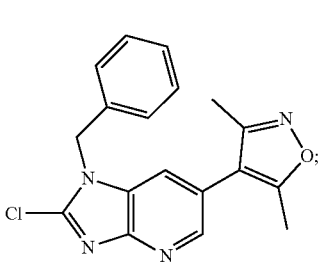

and (d) reacting Compound F:

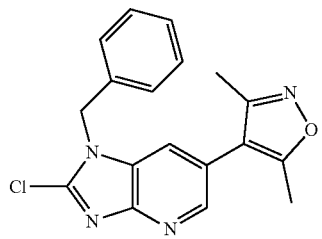
(Compound F)

with methylamine.

27. The process of embodiment 26, wherein step (a) is performed in the presence of a transition metal catalyst and a base.

28. The process of embodiment 27, wherein the transition metal catalyst is a palladium catalyst.

29. The process of embodiment 28, wherein the palladium catalyst is Pd(PPh$_3$)$_4$.

30. The process of embodiment 27, wherein the base is an alkali metal carbonate.

31. The process of embodiment 27, wherein the base is K$_3$PO$_4$.

32. The process of embodiment 26, wherein the first reagent in step (b) is carbonyldiimidazole (CDI), and step (b) is performed in a solvent.

33. The process of embodiment 32, wherein the solvent is an aprotic solvent.

34. The process of embodiment 32, wherein the solvent is DMSO.

35. The process of embodiment 32, wherein step (b) comprises addition of water to the reaction mixture and precipitation of Compound E.

36. The process of embodiment 26, wherein step (c) is performed in the presence of a base.

37. The process of embodiment 36, wherein the chlorination agent is phosphoryl chloride (POCl$_3$).

38. The process of embodiment 36, wherein the base is N,N-diidopropylethylamine (DIPEA).

39. The process of embodiment 36, wherein 4-5 or 8-9 molar equivalents of POCl$_3$ and 1.0-1.1 or 2.5 molar equivalents of DIPEA are used relative to Compound E.

40. The process of embodiment 36, further comprising co-distillation with ethyl acetate prior to quenching the reaction with NaHCO$_3$ solution.

41. The process of embodiment 36, wherein Compound F is isolated by crystallization from an ethyl acetate/n-heptane mixture.

42. The process of embodiment 26, wherein step (d) is performed using methylamine 2 M in THF.

43. The process of embodiment 26, wherein step (d) is performed at 20-30° C.

44. The process of embodiment 26, wherein step (d) further comprises a reaction work-up, comprising dissolving the crude product in an aqueous HCl solution and washing with a non-polar solvent, followed by neutralization with aqueous NaOH solution.

45. The process of embodiment 26, wherein step (d) further comprises removal of any remaining HCl, comprising dissolving the dried material in ethanol, treatment with a solution of sodium hydroxide in ethanol, followed by addition of water to precipitate the product.

46. The process of embodiment 26, wherein Compound C is prepared by (e) reacting Compound B:

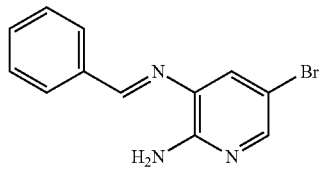
(Compound B)

with NaBH$_4$ in a solvent.

47. The process of embodiment 46, where in the solvent is an alcohol.

48. The process of embodiment 46, wherein the solvent is ethanol.

49. The process of embodiment 46, wherein 0.6 molar equivalents of NaBH$_4$ is used relative to Compound B.

50. The process of embodiment 46, further comprising a work-up and isolation comprising adding an HCl solution to quench the reaction followed by addition of water to precipitate Compound C.

51. The process of embodiment 46, wherein Compound B is prepared by reacting Compound A:

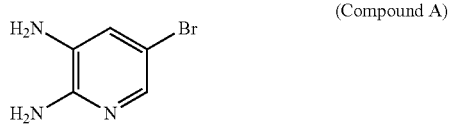
(Compound A)

with benzaldehyde in the presence of an acid.

52. The process of embodiment 51, wherein the acid is acetic acid.

53. The process of embodiment 51, further comprising a solvent, wherein the solvent is methanol.

54. The process of embodiment 51, further comprising adding NaHCO$_3$ solution to the reaction mixture after reaction completion to precipitate Compound B.

EXAMPLES

General methods: The FT-IR of compound I was obtained on a Nicolet 380 FT-IR spectrophotometer. The TGA analysis was conducted on a TA Q5000 instrument thermogravimetric analyzer. The DSC analysis was conducted on a TA Q2000 instrument differential scanning calorimeter from 30-300° C. at 10° C./min. The XRPD pattern of Compound I was obtained on a Bruker instrument D8 advance diffractometer or similar, using mostly the following settings: 40 KV, 40 mA, K$_a$=1.5406 A (Cu—K$_a$ radiation tube), scan scope 4-40 deg. 2 theta, 15 rpm, 10 deg./min. The NMR experiments were recorded on a Bruker AV400 MHz Spectrometer.

Example 1: Synthesis of 5-Bromo-N$^3$-(phenyl methylene)pyridine-2,3-diamine (Compound B)

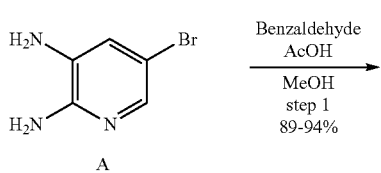

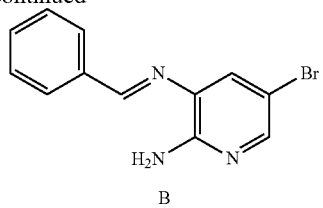

B

Compound A (12.47 kg) was dissolved in methanol (100 kg) and acetic acid (2.3 kg) in a reactor. The solution was cooled to 0-5° C. and stirred for 0.5-1 hour, and benzaldehyde (56.4 g) was added dropwise over 2 hours. Once the reaction was complete (5-10 hours), water (53 kg) was added over 2 hours, and an NaHCO₃ solution (7% in water) was added dropwise over 2 hours, keeping the temperature low (0-5° C.). The mixture was stirred for 3 hours. The solid was filtered off and washed with methanol/water 1:1, followed by drying, leaving Compound B in 94% yield and +99% purity by HPLC. ¹H-NMR (DMSO-d₆): δ8.75 (1H), 8.04 (2H), 7.93 (1H), 7.65 (1H), 7.50-7.60 (3H).

Example 2: Synthesis of N³-Benzyl-5-bromopyridine-2,3-diamine (Compound C)

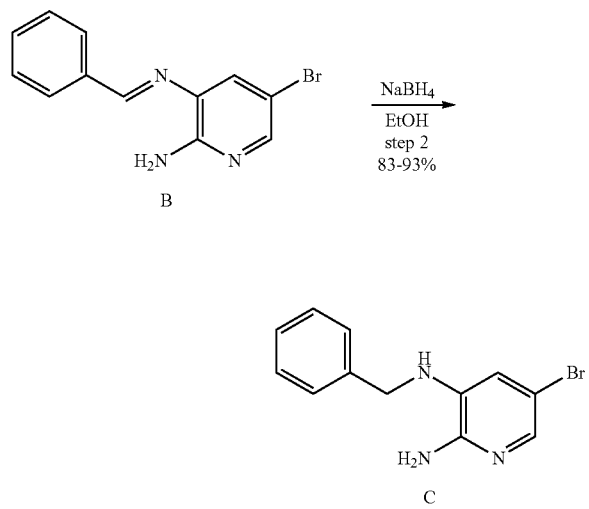

Compound B (17.1 kg) was dissolved in ethanol (140 kg) and NaBH₄ (1.4 kg) was added in portions keeping the temperature between 15-25° C. The reaction mixture was stirred for 8-15 h until the reaction was complete as monitored by HPLC. An HCl solution (2N, 12 kg) was added, adjusting pH to 6-7, followed by adding water (350 kg) dropwise over 5 hours, keeping the temperature between 15-25° C. The mixture was stirred for 1-5 h, filtered and washed with an ethanol/water mixture (1:1 ratio, 50 kg). The solid was dried at ~60° C. for 15-20 h, to afford Compound C (Yield: 14.35 kg (83%), Purity: 99%). ¹H-NMR (DMSO-d₆): δ7.2-7.4 (6 H), 6.55 (1 H), 5.70-5.83 (3 H), 4.30 (2 H).

Example 3: Synthesis of N³-Benzyl-5-(3,5-dimethyl-1,2-oxazol-4-yl)pyridine-2,3-diamine (Compound D)

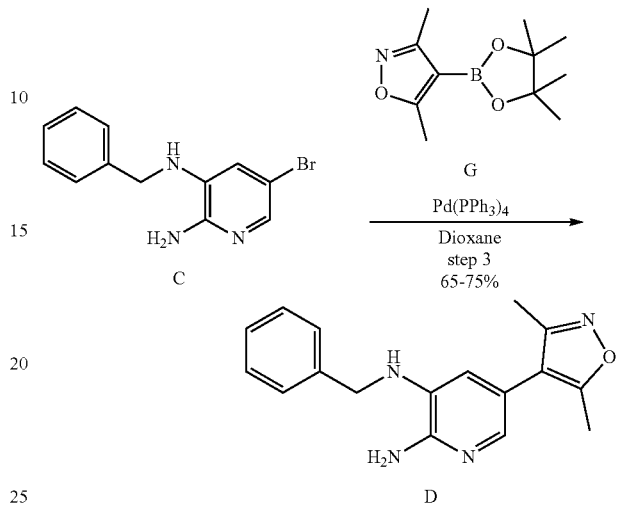

Compound C (14.2 kg), Compound G (14.8 kg), and potassium phosphate tribasic trihydrate (22.0 kg) were mixed followed by addition of 1,4-Dioxane (145 kg) and water (28 kg) and stirred for 1-2 hours. The resulting mixture was thoroughly purged with nitrogen. Tetrakis(triphenylphosphine)palladium(0) (2.9 kg) was added, the solution thoroughly purged with nitrogen, and heated to 90-95° C. until the ratio of Compound C to Compound D was not more than 1% measured by HPLC (16-20 hours). After cooling to 20-30° C., the reaction mixture was filtered, the solid washed with 1,4-dioxane (25 kg), the aqueous phase was removed, and the organic phase was concentrated. Water (96 kg) was added dropwise at 40-45° C., the mixture was cooled to 20-25° C., and the mixture was stirred 1-2 hours until the amount of Compound D remaining in the mother liquors was not more than 0.5%. Compound D was isolated by filtration and sequentially washed with 1,4-dioxane/water (1:2 ratio, 25 kg) and t-butylmethyl ether (27 kg). The wet cake was mixed in methylene chloride (658 kg) at 40-45° C. until all solids dissolved and silica gel (7.0 kg) was added. After stirring for 0.5-1 hour, the mixture was cooled to 20-25° C., filtered, washed with dicholomethane (85 kg), then concentrated. The mixture was cooled and t-butylmethyl ether (56 kg) was added dropwise at 35-40° C. The reactor was cooled to 5-10° C. and stirred for 2-3 hours. The product was isolated by filtration, washed with methyl-t-butyl ether, and dried until the methylene chloride, t-butylmethyl ether, and moisture levels are not more than 0.5%, to obtain Compound D (Yield: 9.7 kg (65%), Purity: 99%). ¹H-NMR (DMSO-d₆): δ7.30-7.45 (4 H), 7.20-7.25 (2 H), 6.35 (1 H), 5.65-5.80 (3 H), 4.30-4.40 (2 H), 2.15 (3 H), 1.95 (3 H). Alternatively, the wet cake obtained after washing sequentially with 1,4-dioxane/water and MTBE can be purified using an ethanol (5 vol.) slurry at 30-40° C. for 1-3 hours, followed by drying until the moisture levels are not more than 0.5% and the ethanol levels are not more than 0.5%.

Example 4: Synthesis of 1-Benzyl-6-(3,5-dimethyl-1,2-oxazol-4-yl)-3H-imidazo[4,5-b]pyridin-2-one (Compound E)

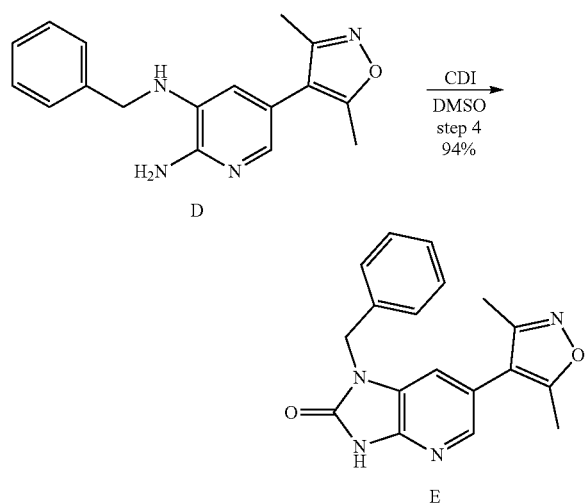

Carbonyldiimidazole solid (8.4 kg) was added (CDI can be added portion wise) to a stirring mixture of Compound D (10.0 kg) and dimethylsulfoxide (35 kg). The mixture was heated to 55-60° C. for 1-3 hours or 35-40° C. until the ratio of Compound D to Compound E was NMT 0.5%. The mixture was cooled to 35-40° C. and water was added over 4 hours. The resulting mixture was stirred at ambient temperature for 3 h. The product was isolated by filtration and washed with water. The dimethylsulfoxide was verified to be NMT 0.5% before drying using heat and vacuum. Drying was complete when the moisture level was NMT 0.5%. Compound E was obtained Yield: 9.8 kg, 94%, Purity: 99.9%). 1H-NMR (DMSO-$d_6$): δ11.85 (1 H), 7.90 (1 H), 7.20-7.45 (6 H), 5.05 (2 H), 3.57 (3 H), 2.35 (3 H), 2.15 (3 H).

Example 5: Synthesis of 4-[1-Benzyl-2-chloro-1H-imidazo[4,5-b]pyridine-6-yl]-3,5-dimethyl-1,2-oxazole (Compound F)

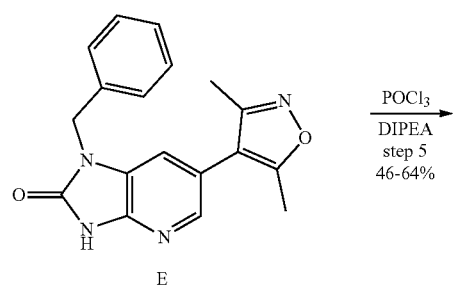

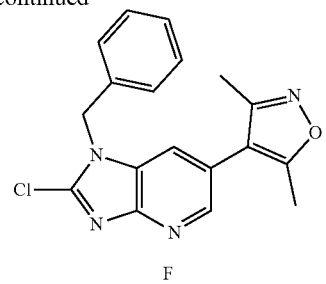

Compound E (9.6 kg) and phosphorus oxychloride (40 kg) were mixed and then treated with diisopropylethyl amine (DIPEA) (9.8 kg) dropwise at 50° C. The resulting mixture was heated to 95-100° C. for 60-70 hours. After the reaction was complete, the mixture was concentrated then cooled. Ethyl acetate was added and the mixture was concentrated under vacuum 3 times, co-distilling with ethyl acetate. Ethyl acetate (EtOAc) (114 kg) was added to the concentrate, the mixture was cooled to ambient temperature, and then added to aqueous sodium bicarbonate (7%) slowly, keeping the mixture 15-25° C. The organic phase was separated and the organic layer was washed twice with aqueous sodium bicarbonate (7%) and then water. The organic phase was concentrated, ethyl acetate (288 kg) was added, and the mixture was concentrated to assure that the moisture level was not more than 0.2%. The mixture in ethyl acetate was decolorized with carbon (CUNO, contained 1.2 kg activated carbon). The mixture was concentrated and n-heptane (23 kg) was added. The product was isolated by filtration and dried under vacuum. Drying was complete when residual moisture, ethyl acetate, and n-heptane were not more than 0.5%. Compound F was obtained (4.95 kg, 46%, Purity: 95%). $^1$H-NMR (MeOH-$d_4$): δ8.40 (1 H), 7.90 (1 H), 7.25-7.45 (5 H), 5.65 (2 H), 2.37 (3 H), 2.22 (3 H).

Example 6: 1-Benzyl-6-(3,5-dimethyl-1,2-oxazol-4-yl)-N-methyl-1H-imidazo[4,5-b]pyridine-2-amine (Compound I)

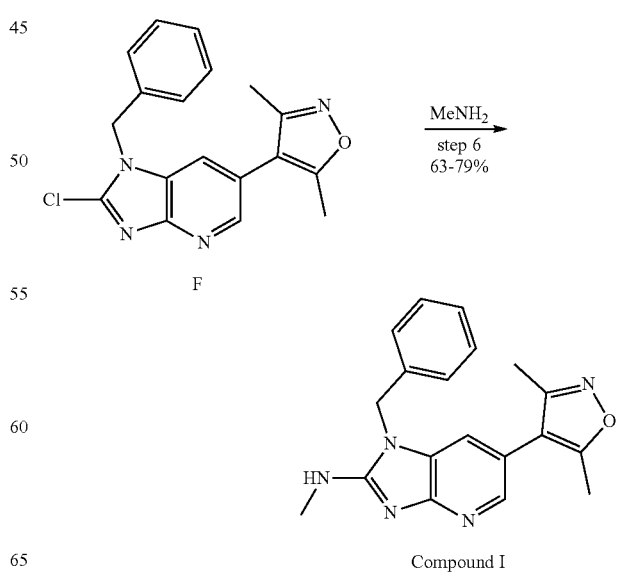

Compound I

Compound F (4.54 kg) was mixed with methylamine in tetrahydrofuran (THF) (31.9 kg, 2 M) and stirred at ambient temperature until the ratio of Compound F to Compound I was NMT 0.1% by HPLC. After reaction completion, the mixture was concentrated under vacuum, water (34 kg) was added dropwise to maintain ambient temperature, stirred for 1-1.5 hours, and the product isolated by filtration. The filter cake was washed with water. The wet cake was placed in a reactor and water (17 kg) was added, and hydrochloric acid (36 kg, 35%) was added and stirred for 2 hours to dissolve the solids. The resulting solution was washed twice with methylene chloride to remove impurities. The aqueous solution was neutralized by adding a sodium hydroxide solution (14.5 kg, 15%) dropwise over 1.5 hours, and stirred for 5 hours. Compound I was isolated by filtration, washed with water, and dried under vacuum. If needed to remove any remaining hydrochloric acid, the dried material was dissolved in ethanol (13.4 kg), treated with a solution of sodium hydroxide in ethanol (0.2 kg NaOH in 4 kg ethanol), and stirred for 1 hour, followed by addition of 70 kg water to precipitate the product. Compound I was isolated by filtration, washed with water, and dried. If needed, Compound I may be further purified by a slurry in hot water.

The dry Compound I was dissolved in ethanol (16.2 kg), and the resulting solution was filtered into a clean room. The ethanol solution was azeotropically dried with absolute ethanol. The resulting mixture was heated to dissolve the product and concentrated. The mixture was heated to reflux dissolve any solid and was cooled slowly with seeding (Compound I—Form VII). The mixture was stirred at 50-60° C. for 10 h. XRPD indicated Form VII. The mixture was further cooled to 45-50° C. and stirred at 45-50° C. for 3 h, solid XRPD indicated it was Form VII. T-butylmethyl ether (MTBE) (26 kg) was added dropwise at 45-50° C. for at least 4 h and stirred for 1 h at 45-50° C. The mixture was cooled to 20-30° C. for 3 h and stirred at 20-30° C. for 2 h. The solid was filtered and rinsed with MTBE and dried to afford Compound I—Form VII (2.82 kg, 63%. Purity >99%). 1H-NMR (DMSO-$d_6$): δ7.96 (d, 1H, J=2.0 Hz), 7.42 (d, 1H, J=2.0 Hz), 7.37 (q, 1H, J=4.2 Hz), 7.32 (m, 2H), 7.26 (m, 1H), 7.24 (m, 2H), 5.30 (s, 2H), 3.00 (d, 3H, 4.5 Hz), 2.34 (s, 3H), 2.16 (s, 3H). 13C-NMR (DMSO-d6): d 164.8, 158.4, 157.7, 156.0, 141.1, 136.4, 128.6 (2C), 127.5, 127.4, 127.2 (2C), 115.8, 114.2 (2C), 44.5, 29.3, 11.2, 10.3). Alternatively, MTBE may be added before adding seed crystals of Compound I—Form VII to the mixture.

What is claimed is:

1. A process of preparing crystalline Compound I, Form VII:

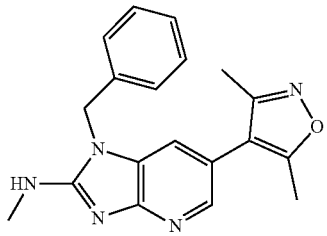
(Compound I)

comprising precipitating Compound I, Form VII from a solution comprising Compound I and ethanol, t-butylmethylether (MTBE), or a mixture thereof.

2. The process of claim 1, wherein the precipitation of Compound I, Form VII is carried out by
   (1) cooling the ethanol solution of Compound I;
   (2) adding seed crystals of Compound I, Form VII to the solution;
   (3) stirring the mixture for about 10 h;
   (4) cooling the mixture further and adding MTBE; and
   (5) stirring for about 3-5 h to precipitate Compound I, Form VII.

3. A process of preparing Compound I, Form VII

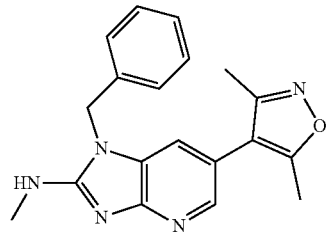
(Compound I)

comprising steps (a)-(e):
(a) reacting Compound C

(Compound C)

with Compound G:

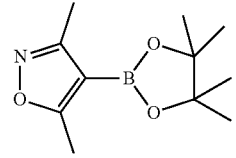
(Compound G)

to produce Compound D:

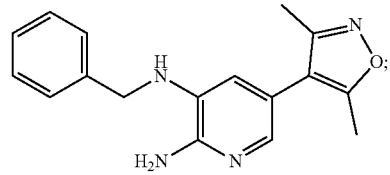
(Compound D)

(b) reacting Compound D:

(Compound D)

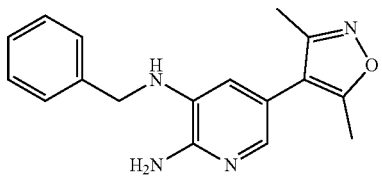

with a first reagent to produce Compound E:

(Compound E)

(c) reacting Compound E:

(Compound E)

with a chlorination agent to produce Compound F:

(Compound F)

(d) reacting Compound F:

(Compound F)

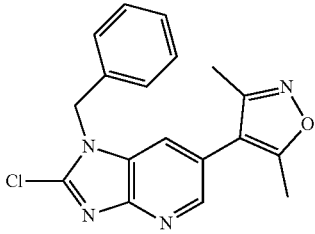

with methylamine to produce Compound I (Compound I)

and (e) precipitating Compound I Form VII from a solution comprising Compound I and ethanol, t-butylmethylether (MTBE), or a mixture thereof.

4. The process of claim 3, wherein step (a) is performed in the presence of a transition metal catalyst and a base.

5. The process of claim 4, wherein the transition metal catalyst is a palladium catalyst.

6. The process of claim 4, wherein the base is an alkali metal carbonate.

7. The process of claim 3, wherein the first reagent in step (b) is carbonyldiimidazole (CDI), and step (b) is performed in a solvent.

8. The process of claim 7, wherein the solvent is an aprotic solvent.

9. The process of claim 7, wherein step (b) comprises addition of water to the reaction mixture and precipitation of Compound E.

10. The process of claim 3, wherein step (c) is performed in the presence of a base.

11. The process of claim 10, further comprising co-distillation with ethyl acetate prior to quenching the reaction with NaHCO₃ solution.

12. The process of claim 10, wherein Compound F is isolated by crystallization from an ethyl acetate/n-heptane mixture.

13. The process of claim 3, wherein step (d) is performed at 20-30° C.

14. The process of claim 3, wherein step (d) further comprises a reaction work-up, comprising dissolving the crude product in an aqueous HCl solution and washing with a non-polar solvent, followed by neutralization with aqueous NaOH solution.

15. The process of claim 3, wherein step (d) further comprises removal of any remaining HCl, comprising dissolving the dried material in ethanol, treatment with a solution of sodium hydroxide in ethanol, followed by addition of water to precipitate the product.

16. The process of claim 3, wherein Compound C is prepared by (f) reacting Compound B:

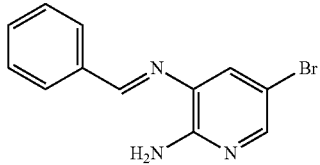
(Compound B)

with NaBH₄ in a solvent.

17. The process of claim 16, where in the solvent is an alcohol.

18. The process of claim 16, further comprising a work-up and isolation comprising adding an HCl solution to quench the reaction followed by addition of water to precipitate Compound C.

19. The process of claim 16, wherein Compound B is prepared by (g) reacting Compound A:

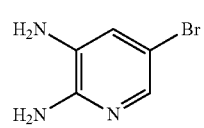
(Compound A)

with benzaldehyde in the presence of an acid.

20. The process of claim 19, further comprising adding NaHCO₃ solution to the reaction mixture after reaction completion to precipitate Compound B.

21. The process of claim 3, wherein the precipitation of Compound I, Form VII is carried out by:
 (1) cooling the ethanol solution of Compound I;
 (2) adding seed crystals of Compound I, Form VII to the solution;
 (3) stirring the mixture for about 10 h;
 (4) cooling the mixture further and adding MTBE; and
 (5) stirring for about 3-5 h to precipitate Compound I, Form VII.

* * * * *